United States Patent [19]

Takita et al.

[11] Patent Number: 4,578,404

[45] Date of Patent: * Mar. 25, 1986

[54] PHARMACEUTICAL COMPOSITION FOR TREATING NEPHRITIS AND METHOD FOR TREATING NEPHRITIS

[75] Inventors: Hitoshi Takita; Sakuo Noda, both of Tokyo; Yutaka Mukaida, Moroyama; Hidetoshi Kobayashi, Tokyo, all of Japan

[73] Assignee: Kureha Kagaku Kogyo Kabushiki Kaisha, Tokyo, Japan

[*] Notice: The portion of the term of this patent subsequent to Mar. 22, 2000 has been disclaimed.

[21] Appl. No.: 597,601

[22] Filed: Apr. 6, 1984

[30] Foreign Application Priority Data

Apr. 15, 1983 [JP] Japan ................... 58-66674

[51] Int. Cl.⁴ ........................... A61K 31/195
[52] U.S. Cl. ................... 514/567
[58] Field of Search ............ 424/319; 514/567

[56] References Cited

U.S. PATENT DOCUMENTS

| | | | |
|---|---|---|---|
| 4,163,060 | 7/1979 | Hartog et al. | 424/319 |
| 4,377,594 | 3/1983 | Takita et al. | 424/319 |
| 4,382,955 | 5/1983 | Takita et al. | 424/319 |
| 4,396,627 | 8/1983 | Ainsworth et al. | 424/319 |
| 4,464,396 | 8/1984 | Takita et al. | 424/319 |

FOREIGN PATENT DOCUMENTS 0041826 12/1981 European Pat. Off. .
0041827 12/1981 European Pat. Off. .

OTHER PUBLICATIONS

Chemical Abstracts; vol. 96 (1982) #162197d; Takita et al.
Chemical Abstracts; vol. 96 (1982) #162198e; Takita et al.

Primary Examiner—Leonard Schenkman
Assistant Examiner—Joseph A. Lipovsky
Attorney, Agent, or Firm—Oblon, Fisher, Spivak, McClelland & Maier

[57] ABSTRACT

Disclosed herein are a pharmaceutical composition for treating nephritis, comprising at least one compound selected from the group consisting of the derivatives of N-(dihdyroxybenzylidene)amino acid, represented by the formula (I):

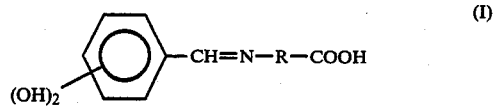

(I)

wherein R represents an alkylene group having one to five carbon atoms, a phenylene group or

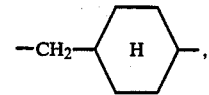

the pharmaceutically acceptable salts and esters thereof, and a pharmaceutically acceptable carrier therefor, and the method for treating nephritis.

8 Claims, 3 Drawing Figures

PHARMACEUTICAL COMPOSITION FOR TREATING NEPHRITIS AND METHOD FOR TREATING NEPHRITIS

BACKGROUND OF THE INVENTION

The present invention relates to a pharmaceutical composition comprising as an active ingredient at least one compound selected from the group consisting of the derivatives of N-(dihydroxybenzylidene)amino acid represented by the formula (I):

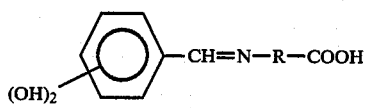

wherein R represents an alkylene group having one to five carbon atoms, a phenylene group or

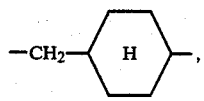

the pharmaceutically acceptable salts and esters thereof, and a pharmaceutically acceptable carrier therefor, and to a method for treating nephritis which comprises administering to a patient suffering from nephritis a pharmaceutically effective amount of a compound selected from the group consisting of the derivatives of N-(dihydroxybenzylidene)amino acid, represented by the formula (I):

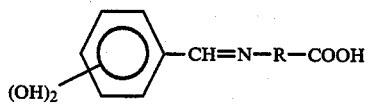

wherein R represents an alkylene group having one to five carbon atoms, a phenylene group or

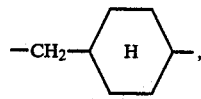

or the pharmaceutically acceptable salts and esters thereof.

The present inventors have already found that the compound represented by the formula (I) wherein R represents

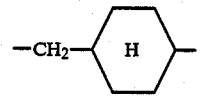

is useful as a medicine and is effective for treatment of auto-immune diseases such as rheumatoid arthritis and systemic lupus erythematosus (refer to Japanese Patent Applications Laid-Open No. 57-116035 (1982) and No. 57-140714 (1982)). Thereafter, as a result of the present inventors' studies on the action of the compounds represented by the formula (I) on human nephritis, it has been found by the present inventors that the compounds represented by the formula (I) inhibit the glomerulonephritis which is regarded as a disease caused by an immuno-complex, and is effective as a medicine for treating nephritis.

Although the cause of diseases due to immunocomplexes such as nephritis is complicated and there are many points not yet elucidated therein, it is considered that the complex of an antigen and an antibody deposit on the glomeruli releasing various chemical mediators which cause disturbance in the renal tissue.

The present inventors have found out that administration of the compounds represented by the formula (I) to a MRL/1 mouse which is an animal naturally suffering from an auto-immune disease suppresses the deposition of immunocomplexes in the glomeruli of the mouse with inhibition of the hyperplastic nephritis such as basement membrane thickening. The present inventors have also found that the above-mentioned compounds clinically reduces the concentration of proteins in the urine of the mouse and that the BSA-nephritis, which is caused by intravenous injection of bovine serum (BSA) into a rabbit, is remarkably improved by the compounds represented by the formula (I), and thus the present inventors have attained the present invention.

SUMMARY OF THE INVENTION

In a first aspect of the present invention, there is provided a pharmaceutical composition for treating nephritis, comprising at least one compound selected from the group consisting of the derivative of N-(dihydroxybenzylidene)amino acid represented by the formula (I):

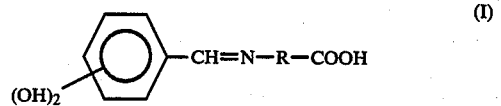

wherein R represents an alkylene group having one to five carbon atoms, a phenylene group or

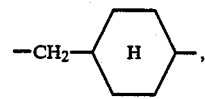

the pharmaceutically acceptable salts thereof, pharmaceutically acceptable esters thereof, and a pharmaceutically acceptable carrier therefor.

In a second aspect of the present invention, there is provided a method for treating nephritis which comprises administering to a patient suffering from nephritis a pharmaceutical effective amount of at least one compound selected from the derivatives of N-(dihydroxybenzylidene)amino acid represented by the formula (I):

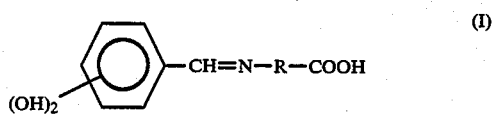

wherein R represents an alkylene group having one to five carbon atoms, a phenylene group or

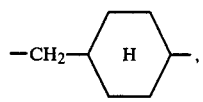

the pharmaceutical acceptable salts and esters thereof.

DETAILED DESCRIPTION OF THE INVENTION

Figure 1:
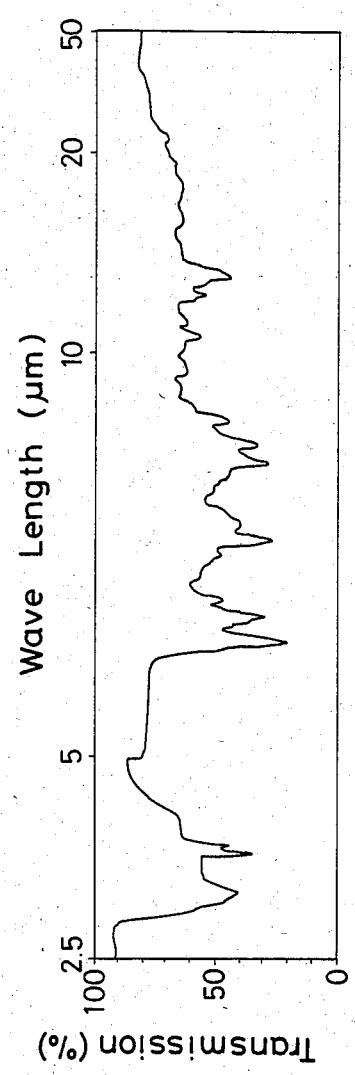
FIGS. 1 to 3 represent, respectively, the infrared absorption spectra of trans-4-[N-(2',5'-dihydroxybenzylidene)aminomethyl]cyclohexane-1-carboxylic acid, 4-[N-(3',4'-dihydroxybenzylidene)amino]benzene-1-carboxylic acid and N-(3',4'-dihydroxybenzylidene)aminocaproic acid.

The pharmaceutical composition for treating nephritis according to the present invention contains as an active ingredient the derivatives of N-(dihydroxybenzylidene)amino acid, represented by the formula (I), the pharmaceutically acceptable salts or esters thereof (hereinafter referred to as "the present compounds"), wherein R is a straight-chain alkylene group having one to five carbon atoms or branched-chain alkylene group having one to five carbon atoms, a phenylene group or

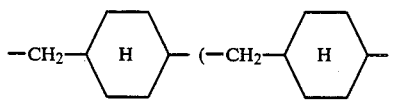

may be in either the trans form or the cis form). The pharmaceutically acceptable esters thereof mean those non-toxic lower alkyl esters of the above-mentioned carboxylic acid. As the alkyl group of the esters, straight-chain alkyl groups having one to three carbon atoms or branched-chain alkyl groups having one to three carbon atoms, for instance, methyl group, ethyl group, n-propyl group or isopropyl group, may be mentioned. The pharmaceutically acceptable salts thereof means the appropriate inorganic salts or organic salts thereof. As the basic material for preparing the above-mentioned pharmaceutically acceptable salt, a hydroxide, carbonate and hydrogen carbonate of an alkali metal such as sodium and potassium and an alkaline earth metal such as calcium and magnesium, ammonia, primary amines, secondary amines and tertiary amines may be mentioned.

The present compound may be synthesized by condensing dihydroxybenzaldehyde with an amino acid, or the ester of the amino acid. As the dihydroxybenzaldehyde, for instance, 2,3-dihydroxybenzaldehyde; 2,4-dihydroxybenzaldehyde, 2,5-dihydroxybenzaldehyde; 2,6-dihydroxybenzaldehyde and 3,4-dihydroxybenzaldehyde may be mentioned. As the amino acid, glycine, ε-aminocaproic acid, aminobenzoic acid, aminomethylcyclohexanecarboxylic acid and the esters thereof may be mentioned.

The condensation is carried out in an organic solvent at a temperature of lower than 150° C., preferably at 0° to 120° C. in an inert gaseous atmosphere. In the case of a reaction temperature of over 150° C., since the reaction is accompanied by various side reactions resulting in reduction of the yield of the desired compound, it is not favorable. Although the organic solvent used in the condensation is not specifically limited so far as it does not participate the reaction, in general, a lower alkanol such as methanol and ethanol, or benzene, toluene, N,N-dimethylformamide, acetonitrile, etc. can be used.

Since the condensation reaction involves dehydration, the reaction is carried out by a method of removing the water formed in the reaction under a reflux condenser or in the presence of a dehydrating agent. Further, an anhydrous lower alcohol such as methanol and ethanol is used as the solvent and the dehydrating agent. After the reaction is over, the reaction mixture is treated by a known method to isolate the present compounds.

The salt according to the present invention can be synthesized by neutralizing the compound represented by the formula (I) with the above-mentioned basic material. For instance, in the case of obtaining a sodium salt of the compound represented by the formula (I), the derivative of N-(dihydroxybenzylidene)aminocarboxylic acid is neutralized with an aqueous solution of sodium hydroxide in an inert atmosphere at a temperature of lower than 100° C., ordinarily at 0° to 50° C. to obtain the sodium salt thereof.

In the case where each of the present compounds was orally administered to a Jc1-ICR mouse at a dose rate of 3000 mg/kg body weight, no abnormal symptom was observed in the mouse.

The present compound can be used as a composition together with a pharmaceutically acceptable carrier and/or an adjuvant, in various types of formulated compositions, administered orally, intraintestinally or injectively. In this case, not less than two kinds of the present compounds can be used in combination, and may be combined with another active ingredients.

As the form of the pharmaceutical composition comprising the present compound, pellets, sublingual pellets, powder, capsules, trouches, aqueous solution, oil solution, suspension, emulsion, syrups, aqueous injection, or oily injections may be mentioned.

As the above-mentioned carrier, water, gelatin, lactose, starch, pectin, magnesium stearate, stearic acid, talc, vegetable oil, arabic gum, polyalkylene glycol, vaseline, sorbitan trioleate, polyoxyethylene sorbitan mono-oleate, alkyl-phenol, aliphatic alcohols, polyvinylpyrrolidone may be mentioned. Further, on formulating the pharmaceutical composition of the present compound, ordinary adjuvants for formulation such as sweetenings, seasonings, coloring agents, preservatives, salts for adjusting osmotic pressure, buffers, etc. may be added.

The content of the present compound in the pharmaceutical composition is in the range of 0.01 to 100% by weight, preferably in the range of 0.05 to 80% by weight.

The pharmaceutical composition for treating nephritis according to the present invention may be administered orally or parenterally to human and animal, and preferably orally. Oral administration includes sublingual administration. Parenteral administration includes injection (for instance, subcutaneous, intramuscular, intravenal and drop) and intrarectal administration.

The dose rate of the present compound for treating nephritis depends on the animal species, the age, individual difference and the disease state of the patient; however, in the case of administration to a human being, it is 0.1 to 500 mg/kg/day, preferably 0.5 to 200 mg/kg/day in oral administration and 0.01 to 200 mg/kg/day, preferably 0.1 to 100 mg/kg/day in parenteral administration. The daily dose will be divided into 1 to 4 parts and each part is taken once to four times per day. In some cases, an amount beyond the above-mentioned range may be administered, if necessary.

The present invention will be explained in more detail while referring to the following non-limiting examples.

EXAMPLE 1

Synthesis of trans-4-[N-(3',4'-dihydroxybenzylidene)aminomethyl]cyclohexane-1-carboxylic acid In 30 ml of dehydrated and purified methanol, 1.753 g (12.7 mmol) of 3,4-dihydroxybenzaldehyde were dissolved, and the solution was added dropwise to 1.994 g (12.7 mmol) of trans-4-aminomethylcyclohexane-1-carboxylic acid in a nitrogen atmosphere. The mixture was reacted by heating under reflux for 3 hours. After cooling the reaction mixture to room temperature, the thus precipitated yellowish orange crystals were collected by filtration, washed with methanol and dried in vacuum to obtain 2.9 g of the object product, trans-4-[N-(3',4'-dihydroxybenzylidene)aminomethyl]cyclohexane-1-carboxylic acid (yield of 82.7%).

EXAMPLE 2

Synthesis of cis-4-[N-(3',4'-dihydroxybenzylidene)aminomethyl]cyclohexane-1-carboxylic acid By heating 395 mg (2.86 mmol) of 3,4-dihydroxybenzaldehyde and 450 mg (2.86 mmol) of cis-4-aminomethylcyclohexane-1-carboxylic acid in dehydrated and purified methanol under reflux for one hour, the two reagents were reacted. Methanol was distilled off under reduced pressure from the uniform reaction mixture which was red orange in color to obtain 0.7910 g of yellow powdery product as a residue.

EXAMPLE 3

Synthesis of ethyl trans-4-[N-(3',4'-dihydroxybenzilidene)aminomethyl]cyclohexane-1-carboxylate In 20 ml of methanol, 0.835 g of 3,4-dihydroxybenzaldehyde and 1.2 g of ethyl trans-4-aminomethylcyclohexane-1-carboxylate were dissolved, and the solution was heated under reflux for one hour in a nitrogen atmosphere. After leaving the reaction mixture to stand still for one night at 0° C., the thus precipitated purple plate-like crystals were collected by filtration and dried to obtain 1.525 g of the object compound.

EXAMPLE 4

Synthesis of trans-4-[N-(2',5'-dihydroxybenzylidene)aminomethyl]cyclohexane-1-carboxylic acid The reaction of 1.753 g (12.7 mmol) of 2',5'-dihydroxybenzaldehyde and 1.994 g (12.7 mmol) of trans-4-aminomethylcyclohexane-1-carboxylic acid was carried out in a similar manner to that in Example 1 to obtain 3.43 g of trans-4-[N-(2',5'-dihydroxybenzylidene)aminomethyl]cyclohexane-1-carboxylic acid as powdery crystals yellowish orange in color. The product showed the following physical properties.

1. Melting point (by capillary method) 173.0° to 175.5° C. with decomposition.
2. Elementary analytical data:

|  | C (%) | H (%) | N (%) |
|---|---|---|---|
| Calculated as $C_{15}H_{19}O_4N$: | 64.96 | 6.91 | 5.05 |
| Found: | 64.7 | 6.7 | 4.8 |

3. Mass spectral analytical data: $M^+ = 277$
4. Infrared spectrum: (as KBr-tablet) Refer to FIG. 1.

EXAMPLE 5

Synthesis of 4-[N-(3',4'-dihydroxybenzylidene)amino]benzene-1-carboxylic acid Into a 200 ml-conical flask, 8.00 g (57.92 mmol) of protocatechualdehyde, 7.94 g (57.92 mmol) of p-aminobenzoic acid and 80 ml of methanol were introduced, and the mixture was stirred at room temperature to obtain a transparent red solution. After stirring the solution for 2 hours at room temperature, the mixture was left in a refrigerator for one night to precipitate powdery red crystals, which were collected by filtration and dried to obtain 10.88 g of the object product (yield of 73.0%).

The thus obtained product showed the following physical properties.

1. Melting point (by capillary method): 249.0° to 252.0° C. with decomposition.
2. Elementary analytical data:

|  | C (%) | H (%) | N (%) |
|---|---|---|---|
| Calculated as $C_{14}H_{11}O_4N$: | 65.36 | 4.31 | 5.45 |
| Found: | 65.1 | 4.3 | 5.4 |

Figure 2:
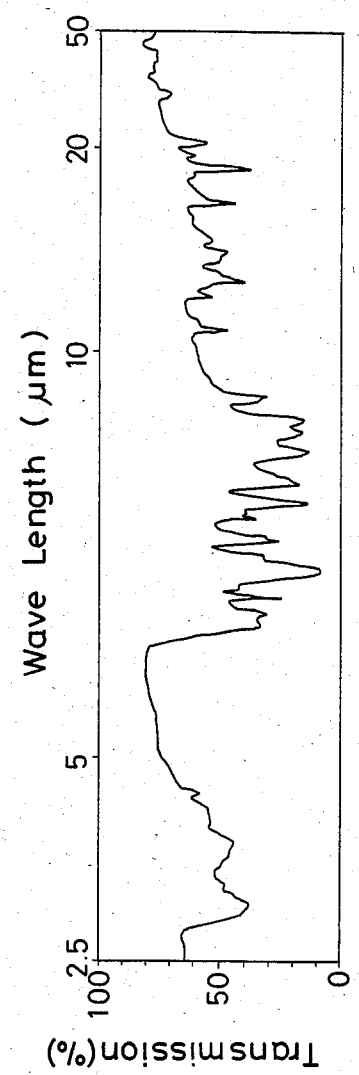

3. Infrared absorption spectrum as a KBr-tablet Refer to FIG. 2.

EXAMPLE 6

Synthesis of N-(3',4'-dihydroxybenzylidene)aminocaproic acid

Into a 200 ml-conical flask, 10.00 g (72.4 mmol) of protocatechualdehyde, 9.50 g (72.4 mmol) of ε-aminocaproic acid and 150 ml of methanol were introduced, and the mixture was heated under reflux while stirring the mixture to obtain a transparent yellow solution. After leaving the solution in a refrigerator for one night, yellow powdery crystals precipitated in the solution. The crystals were collected by filtration and dried to obtain 9.63 g of the object product (yield of 52.9%). The product showed the following physical properties.

1. Melting point (by capillary method): 178.0° to 180.0° C. with decomposition.
2. Elementary analytical data:

|  | C (%) | H (%) | N (%) |
|---|---|---|---|
| Calculated AS $C_{12}H_{17}O_4N$: | 62.14 | 6.82 | 5.58 |
| Found: | 62.4 | 7.0 | 5.5 |

Figure 3:
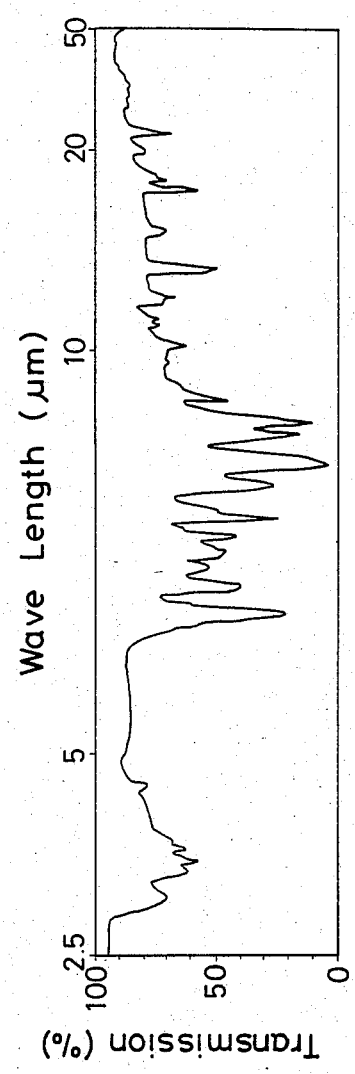

3. Infrared absorption spectrum as a KBr-tablet: Refer to FIG. 3.

EXAMPLE 7

Treatment of MRL/1-mice

The MRL/1-mouse is an animal which naturally develops abnormal auto-immunity and exhibits systemic lupus erythematosus-like lesions such as arthritis and proliferative glomerulonephritis, and the animal gives a high albuminuria in its short life due to the renal disturbance (refer to Exp. Animal, 30(2), pp. 161-172, 1981).

One of the present compounds, trans-4-[N-(3',4'-dihydroxybenzylidene)aminomethyl]cyclohexane-1-carboxylic acid, was orally administered to each of groups of mice which comprise ten male MRL/1-mice 5 weeks after birth, as an aqueous suspension in aqueous 0.3% sodium carboxymethylcellulose solution once a day for 105 to 175 days at a daily dose rate of 100 mg/kg body weight. Another group of ten male MRL/1-mice was used as a control by administering only the aqueous 0.3% solution of sodium carboxymethylcellulose.

When the mice reached the age of 20 to 30 weeks, their renal tissues were surgically removed at various times and examined pathologically with an optical microscope, electron microscope and by a luminescent antibody method. The results on the findings concerning nephritis are shown in Table 1, and the results of the renal pathological findings are shown in Table 2.

In summary, in the group administered with the present compound, an inhibition of occurrence of renal lesion such as the suppression of the deposition of immunocomplex and the proliferative nephritis with hypetrophy of the basal membrane of glomeruli was observed and reduction of albumin in the urine of the treated animals and suppression of a positive test for rheumatic factor were observed.

TABLE 1

| Group | Findings on Nephritis Findings |
|---|---|
| Administered with the present compound* | focal glomerulonephritis |
| Control group | diffuse and proliferative glomerulonephritis together with the hypertrophy of the basal membrane of glomeruli. |

Note:
*Compound No. 1, trans-4-[N—(3',4'-dihydroxybenzylidene)-aminomethyl] cyclohexane-1-carboxylic acid.

EXAMPLE 8

Treatment of MRL/1-mice

The same tests as in Example 7 were carried out by using each of the following present compounds:
trans-4-[N-(2',5'-dihydroxybenzylidene)aminomethyl]-cyclohexane-1-carboxylic acid,
4-[N-(3',4'-dihydroxybenzylidene)amino]benzene-1-carboxylic acid and
N-(3',4'-dihydroxybenzylidene)aminocaproic acid.

As a result, it was found that each of the above-mentioned compounds was effective in inhibiting the occurrence of proliferative nephritis.

EXAMPLE 9

Treatment of artificial glomerulonephritis

To each of several groups of 5 male rabbits (each rabbit is 2-3 kg), an aqueous 1% solution of bovine serum albumin in aqueous physiological saline solution was injected once a day into the auditory vein continuously for 3 months to cause artificial glomerulonephritis with strong albuminuria.

To the rabbit under such a treatment, the same compound as in Example 1, trans-4-[N-(3',4'-dihydroxybenzylidene)aminomethyl]cyclohexane-1-carboxylic acid, as the same aqueous suspension, was orally administered once a day at a daily dose rate of 100 mg/kg body weight continously for 3 months. Thereafter, the thus treated rabbit was sacrificed to remove the renal tissue thereof and examine the renal tissue under an optical microscope and an electron-microscope and by a luminescent antibody method. The same examination was carried out on another group of 5 male rabbits similarly treated with bovine serum albumin, however, not treated with the present compound.

As a result, in the group of the rabbits administered with the present compound, the inhibition of occurrence of albuminuria and urea-form nitrogen in serum was observed together with inhibition of renal lesions as well as suppression of the deposition of immunocom-

TABLE 2

| | Pathological Findings on Kidney | | | | | |
|---|---|---|---|---|---|---|
| | Deposition of immunocomplex on | | Proliferativeness of | | | Rheumatic factor in |
| Group | Basal membrane | Mesangium | Basal membrane | Mesangium | Albuminurea | serum |
| Administered with the present compound No. 1 | + | + | ± | + | + | negative |
| Control | +++ | +++ | ++ | ++ | +++ | positive | plexes onto the glomeruli and of proliferative glomerulonephritis as shown in Table 3.

TABLE 3

| | Findings on the rabbits artificially made to be glomerulonephritic | | | | | |
|---|---|---|---|---|---|---|
| | | BUN(urea-form nitrogen in | Deposition of immunocomplex on glomeruli | | Proliferativeness | |
| Group of rabbits | Albuminuria | serum) (mg/dl) | Basal membrane | Mesangium | Basal membrane | Mesangium |
| Administered with the present compound | ± to + | 15 to 50 | + to ± | + to ± | ± | — |
| Control* | ++++ to +++ | 150 to 200 | +++ | +++ | ++ | ++ |

Note:
*Control: treated with bovine serum albumin, however, not treated with the present compound.

EXAMPLE 10

Preparation of a pharmaceutical composition

By uniformly mixing the following components:

10 parts by weight of trans-4-[N-(3',4'-dihydroxybenzylidene)aminomethyl]cyclohexane-1-carboxylic acid, 15 parts by weight of heavy magnesium oxide and 75 parts by weight of lactose, and pulverizing the thus obtained mixture, a powdery pharmaceutical composition was obtained.

By encapsulating the thus obtained powdery pharmaceutical composition with gelatin, an encapsulated pharmaceutical composition was prepared.

EXAMPLE 11

Preparation of a pharmaceutical composition

By uniformly mixing and kneading the following components:

45 parts by weight of trans-4-[N-(2',5'-dihydroxybenzylidene)aminomethyl]cyclohexane-1-carboxylic acid, 10 parts by weight of starch, 20 parts by weight of lactose, 3 parts by weight of polyvinyl alcohol and 22 parts by weight of water, and after processing the thus kneaded mixture into fine granules, the fine granules were dried and sifted to be a granular pharmaceutical composition.

EXAMPLE 12

Preparation of a pharmaceutical composition

By dissolving 0.6 part by weight of sodium trans-4-[N-(3',4'-dihydroxybenzylidene)aminomethyl]cyclohexane-1-carboxylate in 99.4 parts by weight of aqueous physiological saline solution under heating, a solution was obtained. By sterilizing the thus obtained solution, an injection was obtained.

What is claimed is:

1. A pharmaceutical composition for treating nephritis, comprising 0.01 to 100% by weight of at least one compound selected from the group consisting of the derivatives of N-(dihydroxybenzylidene)amino acid, represented by the formula (I):

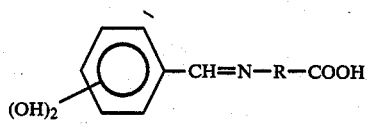

wherein R represents an alkylene group having one to five carbon atoms, a phenylene group or

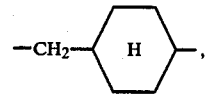

the pharmaceutically acceptable salts thereof and the pharmaceutically acceptable esters thereof and a pharmaceutically acceptable carrier therefor.

2. A pharmaceutical composition according to claim 1, wherein R of the formula (I) is

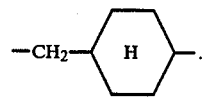

3. The pharmaceutical composition according to claim 1, wherein the content of said compound in the pharmaceutical composition is 0.05 to 80% by weight.

4. A method for treating nephritis, comprising administering to a patient suffering from nephritis at least one compound selected from the group consisting of the derivatives of N-(dihydroxybenzylidene)amino acid represented by the formula (I):

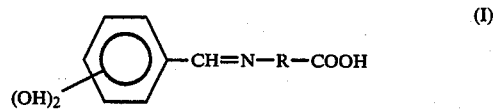

wherein R represents an alkylene group having one to five carbon atoms, a phenylene group or

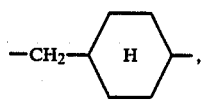

the pharmaceutically acceptable salts thereof and the pharmaceutically acceptable esters thereof, wherein said compound is administered in an amount sufficient to reduce the effects of nephritis, said amount being from about 0.1 to 500 mg/kg/day by oral administration or from about 0.01 to 200 mg/kg/day in parenteral administration.

5. A method for treating nephritis according to claim 4, wherein R of said formula (I) is

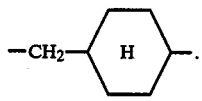

6. The method according to claim 4, wherein a dose of the administration is divided into 1 to 4 parts and each part is taken once to four times per day.

7. The method according to claim 4, wherein said amount is from about 0.5 to 200 mg/kg/day in oral administration.

8. The method according to claim 4, wherein said amount is from about 0.1 to 100 mg/kg/day in parenteral administration.

* * * * *